United States Patent [19]
Buechler et al.

[11] Patent Number: 5,985,579
[45] Date of Patent: *Nov. 16, 1999

[54] ANTIBODIES TO COMPLEXES OF LIGAND RECEPTORS AND LIGANDS AND THEIR UTILITY IN LIGAND-RECEPTOR ASSAYS

[75] Inventors: Kenneth F. Buechler, San Diego; Gunars E. Valkirs, Escondido, both of Calif.

[73] Assignee: Biosite Diagnostics, Inc., San Diego, Calif.

[ * ] Notice: This patent is subject to a terminal disclaimer.

[21] Appl. No.: 08/458,901

[22] Filed: Jun. 2, 1995

Related U.S. Application Data

[60] Division of application No. 08/071,203, Jun. 1, 1993, Pat. No. 5,480,792, which is a continuation-in-part of application No. PCT/US91/06324, Sep. 4, 1991, which is a continuation-in-part of application No. 07/583,556, Sep. 14, 1990, abandoned.

[51] Int. Cl.⁶ ..................... G01N 33/566; G01N 33/543; G01N 33/53
[52] U.S. Cl. ................ 435/7.1; 422/56; 422/57; 422/68.1; 435/970; 435/975; 436/501; 436/518; 436/807
[58] Field of Search ............... 422/56, 57, 68.1; 435/7.1, 970, 975; 436/518, 807, 501

[56] References Cited

U.S. PATENT DOCUMENTS

| | | | |
|---|---|---|---|
| 4,200,690 | 4/1980 | Root et al. ................... | 435/7 |
| 4,233,402 | 11/1980 | Maggio et al. ............... | 435/7 |
| 4,246,339 | 1/1981 | Cole et al. ................... | 435/7 |
| 4,366,241 | 12/1982 | Tom et al. .................... | 435/7 |
| 4,376,110 | 3/1983 | David et al. ............... | 435/513 |
| 4,391,904 | 7/1983 | Litman et al. ................ | 435/7 |
| 4,446,232 | 5/1984 | Liotta ........................ | 435/7 |
| 4,623,627 | 11/1986 | Huang et al. .............. | 435/240 |
| 4,632,901 | 12/1986 | Valkirs et al. ................ | 435/5 |
| 4,727,019 | 2/1988 | Valkirs et al. ................ | 435/5 |
| 4,732,847 | 3/1988 | Stuart et al. ................. | 435/6 |
| 4,740,468 | 4/1988 | Weng et al. ................... | 435/7 |
| 4,743,542 | 5/1988 | Graham, Jr. et al. ........ | 435/7 |
| 4,828,985 | 5/1989 | Self ....................... | 435/792 |
| 4,849,338 | 7/1989 | Litman et al. ............. | 435/7.1 |
| 4,870,007 | 9/1989 | Smith-Lewis .............. | 435/25 |
| 4,880,731 | 11/1989 | Kasper ..................... | 435/7 |
| 5,089,391 | 2/1992 | Buechler et al. .......... | 435/7.1 |

FOREIGN PATENT DOCUMENTS

| | | | |
|---|---|---|---|
| 0200381 | 4/1986 | European Pat. Off. ........ | 33/549 |
| 0188093 | 7/1986 | European Pat. Off. ........ | 33/543 |
| 0188093 | 1/1991 | European Pat. Off. ........ | 33/543 |
| 0419367 | 3/1991 | European Pat. Off. ........ | 33/53 |
| 8505487 | 9/1986 | United Kingdom . | |
| 8401746 | 5/1985 | WIPO . | |
| 8500120 | 10/1985 | WIPO . | |
| 8401737 | 5/1986 | WIPO . | |
| 8500255 | 11/1986 | WIPO ..................... | 33/531 |

OTHER PUBLICATIONS

Nemazee and Sato, *Proc. Natl. Acad. Sci. USA* 79:3828–3832 (1982).
Zola, *Monoclonal Antibodies: A Manual of Techniques* (CRC Press).
O'Shannessy and Quarles, *J. Immunology Methods* 99:153–161 (1987).

*Primary Examiner*—Michael P. Woodward
*Assistant Examiner*—Mary K Zeman
*Attorney, Agent, or Firm*—Lyon & Lyon LLP

[57] ABSTRACT

Methods and test devices for detecting the presence or amount of target ligand in non-competitive sandwich ligand-receptor assay processes. Antibodies which bind to the complex of ligand receptor and target ligand but do not bind significantly to the ligand receptor and which bind the target ligand with substantially less affinity than the complex are taught and their uses described. These assays can be used to eliminate the "hook" effect in non-competitive sandwich assays. Furthermore, the antibodies are selected and assay methods described so that, as a result of the assay process, no detectable response is observed due to the binding of antibody and ligand receptor in the absence of target ligand.

40 Claims, No Drawings

ANTIBODIES TO COMPLEXES OF LIGAND RECEPTORS AND LIGANDS AND THEIR UTILITY IN LIGAND-RECEPTOR ASSAYS

This application is a divisional of application Ser. No. 08/071,203, filed Jun. 1, 1993, now U.S. Pat. No. 5,480,792, which was a continuation-in-part of PCT/US91/06324 filed Sep. 4, 1991, which was a continuation-in-part of application Ser. No. 07/583,556 filed Sep. 14, 1990 (now abandoned). Priority is claimed from each of these applications.

FIELD OF THE INVENTION

More particularly, this invention relates to the use of antibodies specific for ligand-receptor complexes in non-competitive ligand-receptor assays. The amount of complexes of ligand receptor and target ligand bound to such antibodies is related to the amount of the target ligand in the sample.

BACKGROUND OF THE INVENTION

As used herein, the term "ligand-receptor assay" refers to an assay for at least one target ligand which may be detected by the formation of a complex between the ligand and a receptor capable of specific interaction with that target ligand. The target ligand may be the analyte itself or a substance which, if detected, can be used to infer the presence of the analyte in a sample. In the context of the present invention, the term "ligand", includes haptens, hormones, peptides, proteins, deoxyribonucleic acid (DNA), ribonucleic acids (RNA), metabolites of the aforementioned materials and other substances of either natural or synthetic origin which may be of diagnostic interest and have a specific ligand receptor therefor. Ligand-receptor assays are generally useful for the in vitro determination of the presence and concentration of ligands in body fluids, food products, animal fluids, and environmental samples. For example, the determination of specific hormones, peptides, proteins, therapeutic drugs, and toxic drugs in human blood or urine has significantly improved the medical diagnosis of the human condition. There is a continuing need for improvements in such assays in order to increase their accuracy and reliability.

Ligand-receptor assays rely on the binding of target ligands by ligand receptors to determine the concentrations of target ligands in a sample. Ligand-receptor assays can be described as either competitive or non-competitive. Competitive assays generally involve a sample suspected of containing target ligand, a ligand analogue conjugate, and the competition of these species for a limited number of binding sites provided by the ligand receptor.

Non-competitive assays generally utilize ligand receptors in substantial excess over the concentration of target ligand to be determined in the assay. Sandwich assays, in which the target ligand is detected by binding to two ligand receptors, one ligand receptor labeled to permit detection and a second ligand receptor, frequently bound to a solid phase, to facilitate separation from unbound reagents, such as unbound labeled first ligand receptor, are examples of non-competitive assays. Methods utilizing two monoclonal antibodies, selected to bind the antigenic substance (target ligand) at sites remote from each other so as to not interfere with the others binding to the antigen, in sandwich assays are described in U.S. Pat. No. 4,376,110. Similar assays for the determination of haptens are described in International Application Number PCT/US84/01737. While such assays are designed so that the concentration of the receptors is each in excess over the concentration of the target ligand in the assay range, some target ligands can be present in samples at concentrations that are substantially higher than the concentrations of receptors employed in the assay. In simultaneous, sandwich assays where the labeled receptor and the unlabeled receptor are mixed together with the sample, a large excess of the target ligand can result in binding of separate target ligand molecules to the labeled receptor and to the unlabeled receptor so that the formation of the sandwich complex of labeled receptor/target ligand/unlabeled receptor is inhibited. The response in such assays can be misinterpreted so that the determination of the target ligand concentration can result in an incorrect concentration, a much lower concentration than is actually present in the sample. This is widely known as the "hook" effect in sandwich assays. Faced with such a possibility, users of such assays routinely assay dilutions of the sample to determine if the dilutions are quantitated linearly (i.e. the concentration of the target ligand determined for the dilution, when multiplied by the dilution factor, is the same as the target ligand concentration determined for the sample). Such additional testing would be unnecessary if the "hook" effect were not a potential problem. The hook effect can be minimized in sandwich assays by choosing sequential assay protocols where the unlabeled receptor is immobilized on a solid phase and the solid phase is washed to remove unbound target ligand after incubation with the sample and before addition of the labeled receptor. Such assay protocols are lengthy and require more steps and manipulation than simultaneous protocols.

The problem of "hook" effects in sandwich assays has been addressed in several ways. In U.S. Pat. No. 4,743,542, a method is described where one of the receptors is labeled for detection and the other receptor is labeled with a hapten so that a receptor for the hapten can be used to bind the hapten-labeled receptor to a solid phase. The invention utilizes either unlabeled first receptor or non-haptenated second receptor to extend the assay range for the target ligand by minimizing the "hook" effect. The requirement for additional receptor is a principal disadvantage of this method because in some cases the concentration of target ligand can be so high that the quantity of additional receptor that is needed to prevent the "hook" effect is not practical. Similarly, the method of U.S. Pat. No. 4,778,751 requires excess receptor coupled to a liquid matrix that can be immobilized on a solid phase. Again, the primary mechanism used to overcome the "hook" effect is the use of large quantities of receptor needed to bind up all of the target ligand, an impractical solution for many target ligands.

In the present invention antibodies are selected that bind the complex of ligand receptor and target ligand (ligand analogue conjugate) and substantially do not bind the ligand receptor or the target ligand when they are not bound to one another. The use of antibodies to ligand receptor-ligand complexes in sandwich assays eliminates or greatly reduces the "hook" effect without the requirement for excessive amounts of such antibodies.

Antibodies that bind the complex of ligand and a specific antibody for the ligand have been described by Nemazee and Sato (Proc. Natl. Acad. Sci. USA, Vol. 79, pp. 3828–3832, 1982). They postulated that three types of antibody are produced in response to immunization with antibody-antigen complexes, antibodies that bind to either conformationally altered antibody or antigen and antibodies that bind to parts of both antibody and antigen. Nemazee and Sato also provide methods for producing antibodies of the first type, antibodies that bind conformationally altered antibody when it is bound to antigen. Johannsson, in UK Patent Application No. 8505487, describes antibodies produced by immunization of the complex of a fragment of specific antibody and its ligand. The resulting antibodies are said to bind the complex of a specific binding fragment and its binding partner with high affinity while binding the specific binding fragment or the binding partner with low affinity. This prior art does not describe methods for selecting and using such antibodies to overcome the "hook" effect in sandwich assays. In the present invention the use of antibodies to complexes of ligands and ligand receptors is described in embodiments that substantially eliminate the "hook" effect in sandwich ligand-receptor assays.

SUMMARY OF THE INVENTION

The present invention provides a means for the detection of the presence or amount of target ligand in non-competitive, sandwich ligand-receptor assay processes. Antibodies that bind to the complex of ligand receptor and target ligand but do not bind to the ligand receptor and bind the target ligand with substantially less affinity than the complex are utilized in non-competitive, sandwich assay processes. Assays utilizing such antibodies are less affected by the presence of high concentrations of target ligand that can cause a "hook" effect. The present invention selects antibodies that exhibit at least 10× greater affinity for the complex of target ligand and ligand receptor than for the target ligand. Furthermore, the antibodies are selected so that as a result of the assay process, no detectable assay response is observed due to the binding of antibody and ligand receptor in the absence of target ligand. The present invention can be used to substantially eliminate the "hook" effect in non-competitive, sandwich assays.

DETAILED DESCRIPTION OF THE INVENTION

The present invention provides a means for the detection of the target ligands in fluids from non-competitive, sandwich ligand-receptor assay processes. The detection of the target ligand in such fluids is accomplished by using antibodies that bind to the complex of the target ligand and a ligand receptor specific for the target ligand. The present invention provides a means for the selection of antibodies that do not bind the ligand receptor and that bind the target ligand with substantially less affinity than the complex of ligand and ligand receptor. Assay processes utilizing such antibodies are described where the "hook" effect is substantially eliminated.

Antibodies for use in the present invention can be generated by immunization using complexes of ligand receptor and ligand as the immunogen. These complexes may be covalently attached to a carrier protein such as keyhole limpet hemocyanin in order to elicit an immune response if they are not immunogenic. For example, hybrid complexes of target oligonucleotides and oligonucleotide probes may be covalently attached to a carrier protein in order to generate antibodies that are specific for the hybrid complex of oligonucleotides.

In the specific case of generating antibodies to the hybrid complex of the target oligonucleotide and oligonucleotide probe, the oligonucleotide probe could have a recognition molecule which allows for an additional affinity of the antibody for the hybrid complex. The recognition molecule, for example, can be incorporated near the hybridization site in the probe sequence or be attached to a base or the backbone, for example, on a linker arm, or can be a modification of a nucleotide. In any of these cases, the presence of the recognition molecule would not affect the hybridization of the probe to the target oligonucleotide or prevent the probe from performing its desired function. Methods for altering probes without affecting their desired function are known in the art and may be adopted to this invention.

In some cases it may be beneficial to covalently link the ligand receptor to the target ligand to stabilize the complex. Such a procedure is normally carried out by first forming the complex of ligand receptor and ligand and then forming the covalent attachment so that the juxtaposition of the ligand receptor and the ligand in the complex is not changed by the covalent attachment but rather is stabilized. Bifunctional crosslinking reagents that can be used to crosslink the ligand receptor and the ligand are known to those skilled in the art. Methods for the immunization of animals are known to those skilled in the art. When polyclonal antibodies are used in the present invention, a preferred method for the isolation of antibodies to the complex of ligand receptor and ligand is affinity chromatography. Methods for the immobilization of the affinity ligand on matrices for affinity chromatography are known to those in the art. Immobilization of the complex of ligand receptor and ligand on an affinity matrix is a preferred method for separating antibodies useful in the present invention from a polyclonal antibody mixture. Because most affinity purification conditions require relatively stringent conditions for the elution of the bound antibodies from the affinity matrix, the stability of the complex of ligand receptor and ligand may be affected by those conditions. Covalent attachment of the ligand receptor to the ligand after the binding complex is formed may be necessary under these circumstances. A particularly preferred method for the affinity purification of antibodies useful in the present invention is the immobilization of the target ligand on the affinity matrix. Such an affinity matrix will bind both antibodies to the target ligand and antibodies to the complex of ligand receptor and target ligand. However, the antibodies specific for the complex of ligand receptor and target ligand will be bound with substantially lower affinity than the antibodies to the target ligand and can be eluted from the affinity matrix under mild conditions that will leave the antibodies to the target ligand bound to the affinity matrix. Polyclonal antibodies that are useful in the present invention must satisfy the selection criteria described below.

Particularly preferred for use in the present invention are monoclonal antibodies. Methods for the generation of monoclonal antibodies are known to those skilled in the art (see, for example, Zola, Heddy, *Monoclonal Antibodies: A Manual of Techniques*, CRC Press). Monoclonal antibodies with the properties required by the present invention can be selected by utilizing assays that select antibodies that do not bind the ligand receptor but do bind the complex of ligand receptor and ligand with substantially greater affinity than their affinity for the ligand.

The antibodies of the present invention include not only intact immunoglobulins but also fragments of immunoglobulins that are derived from intact immunoglobulins. It is also recognized that antibodies or fragments of antibodies can generated by genetic engineering methods from antibody gene sequences. Specific binding species that are produced by such methods that meet the selection criteria and are used according to the present invention are also considered to be antibodies in the context of the present invention.

The antibodies used in the present invention are selected according to their affinity for the ligand receptor-ligand complex relative to their affinity for the ligand. In addition, antibodies to ligand receptor-ligand complexes used in the present invention that do not bind the ligand receptor are selected so that in the final assay format where either antibody or ligand receptor is labeled for detection (to create an antibody conjugate or ligand receptor conjugate, respectively), there is no detectable assay response due to the binding of antibody to ligand receptor. When target ligand, ligand receptor conjugate, and antibody are contacted such that the target ligand is present in substantial excess over the antibody and the antibody is in substantial excess over the ligand receptor conjugate, the binding reactions proceed according to the Law of Mass Action.

$$A+LRC:L=LRC:L:A \text{ and } A+L=A:L$$

At equilibrium, these two binding reactions are characterized by equilibrium constants (affinity constants) given by $$K_L = \frac{[A:L]}{[A][L]} \text{ and } K_{LRC:L} = \frac{[LRC:L:A]}{[A][LRC:L]}$$

where [A] is the concentration of free antibody, [L] is the concentration of free target ligand, [A:L] is the concentration of target ligand bound to antibody, [LRC:L] is the concentration of target ligand bound to ligand receptor conjugate, and [LRC:L:A] is the concentration of target ligand bound to ligand receptor conjugate and to antibody. At equilibrium, the concentration of free antibody must be the same in these expressions and by solving for [A] in one of the equations and substituting into the other equation the following relationship must be satisfied $$\frac{K_{LRC:L}}{K_L} = \frac{[LRC:L:A][L]}{[LRC:L][A:L]}$$

Under conditions of excess ligand, the concentration of free target ligand, [L], is essentially the total concentration of target ligand in the assay mixture and the concentration of target ligand bound to antibody, [A:L] can be estimated by using the total concentration of antibody in the assay mixture. Methods for determining the concentration of antibody added to the assay mixture are well known to those skilled in the art. The ratio of [LRC:L:A]/[LRC:L] is simply the ligand receptor conjugate bound to antibody divided by the ligand receptor conjugate not bound to antibody if the affinity of the ligand receptor for the ligand is such that substantially all of the ligand receptor conjugate is bound to the target ligand. The concentrations of the target ligand and the ligand receptor conjugate must be chosen so that this condition is satisfied. If the concentration of the target ligand is chosen so that it is more than 100× the dissociation constant for the binding of ligand receptor conjugate and ligand under the conditions of the assay, then greater than 99% of the ligand receptor conjugate will be bound to target ligand. To determine the ratio of [LRC:L:A]/[LRC:L], the antibody and ligand receptor conjugate bound to it can be separated from the assay mixture by using antibodies specific for the antibody species being tested. For example, if mouse monoclonal antibodies are being selected for use in the present invention, an antibody raised in goats that is specific for mouse antibodies can be used to selectively precipitate the mouse antibodies and moieties that are bound to them from the assay mixture. Alternatively, the goat antibody specific for mouse antibodies can be attached to a solid phase such as latex particles, and centrifugation or filtration can be used to separate the antibodies from the assay mixture. If the ligand receptor is also a mouse antibody, then the antibody that is being tested can be labeled with a hapten and an antibody specific for that hapten can be used to remove only the antibody that is being tested from the assay mixture. Methods for labeling antibodies without affecting their binding are known to those skilled in the art (see, for example O'Shannessy and Quarles, *Journal of Immunological Methods*, 99, 153–161 (1987)). Under these conditions, the ratio of $K_{LRC:L}/K_L$ can be determined. Antibodies where this ratio exceeds 10 are selected for use in the present invention. The determination of the relative affinity of the antibody for ligand receptor-ligand complex and for ligand is made under conditions that are similar to the conditions that are present when the "hook" effect is normally problematic. Thus, the selection criteria described here are effective in selecting antibodies to ligand receptor-ligand complexes that substantially eliminate the "hook" effect.

The antibody selected by the assay described above can be used in assay processes to bind the complex of target ligand and ligand receptor conjugate. Alternatively, the antibody can be coupled to a signal development element to form an antibody conjugate. The antibody conjugate can be used in assay processes to bind the complex of target ligand and ligand receptor.

The assay described above can also be used to select antibodies that do not bind to the ligand receptor by determining if ligand receptor conjugate binds to the antibody being tested in the absence of target ligand. The absence of binding between the antibody and the ligand receptor conjugate in the above assay is an indication that there is no binding between the two species. However, because the binding reactions are subject to the Law of Mass Action, the concentrations of the antibody and the ligand receptor in the final assay format are variables that substantially affect the binding of antibody to ligand receptor. Therefore, the final assay format, where either an antibody conjugate or a ligand receptor conjugate is employed must be used to determine that there is no detectable response due to the binding of antibody to ligand receptor. A detectable response is a response that is higher than the response noise due to non-specific binding by a statistically significant margin.

The antibody that is selected by the above procedure is used in non-competitive, sandwich assays for the detection of target ligand in fluid samples. The antibody can be labeled for detection by forming an antibody conjugate where the antibody is coupled to a signal development element or to an element such as a protein that is coupled to a signal development element. Methods for the covalent coupling of antibodies to proteins or to signal development elements such as fluorescent, radioactive, or chemiluminescent labels are known to those skilled in the art. Preferred signal development elements are those which can produce a visual response that is used to detect the presence or amount of target ligand in the sample. Such signal development elements include sol particles that have strong absorbances in the visual spectrum such as colloidal gold, colloidal selenium, colored latex particles, and enzymes that produce colored products when contacted with appropriate substrates. When the antibody conjugate is bound to ligand receptor-ligand complexes, the amount of antibody conjugate-ligand receptor-ligand complex is related to the concentration of target ligand in the sample. A preferred embodiment is one where the ligand receptor is immobilized on a solid phase to facilitate removal of the unbound antibody conjugate from the assay mixture by washing. Alternatively, the ligand receptor and moieties bound to it, such as antibody conjugate bound to the complex of ligand receptor and ligand, can be separated from the assay mixture by utilizing an immobilized receptor for the ligand receptor. The ligand receptor can also be coupled to a hapten or another element for which there is a specific receptor, such as an anti-hapten antibody. The specific receptor can then be used to remove the ligand receptor and moieties bound to it from the assay mixture. These methods, depending upon assay design, can each be utilized successfully to develop assays where the amount of antibody conjugate-ligand receptor-ligand complex is detected and related to the concentration of target ligand in the sample. When antibodies are used that are selected according to the present invention in the assay formats described, the "hook" effect is substantially eliminated.

In the context of the present invention, the term "immobilized" encompasses all physical mechanisms for immobilizing antibodies or receptors such that during the performance of the assay process, substantially all of the antibody or receptor remains in a pre-determined locus. Such mechanisms include covalent binding, non-covalent binding, chemical coupling, physical entrapment of particulates operatively associated with antibodies or receptors, and adsorption by hydrophobic/hydrophobic or hydrophilic/hydrophilic interactions. The immobilization of the antibody or receptor onto the solid support of the solid phase of the present invention may be accomplished in a number of ways. The antibody or receptor may be immobilized by the technique of entrapping antibody-coated or receptor-coated particulates by a porous matrix solid support. Methods for introducing such particulates to a porous matrix are discussed in U.S. Pat. Nos. 4,446,232, 4,740,468 and European Patent Application 86302521.9, incorporated by reference herein. A particularly preferred method of immobilization of the anti-body or receptor onto the solid support wherein the solid support is a porous matrix comprises in part, immobilization of the antibody or receptor on the solid support by covalent or non-covalent chemical binding. Techniques for binding antibodies or receptors to a solid support are well known in the art. A variety of solid supports, including a porous matrix, a non-porous matrix, beads, membranes or filters, may be used in the present invention. Such solid supports can be incorporated into a variety of test devices including dipsticks and devices such as those described in U.S. Pat. Nos. 4,200,690, 4,246,339, 4,366,241, 4,632,901, and 4,727,019. A particularly preferred solid phase is a membrane suspended in a device such that when the assay fluid is contacted with the membrane, the fluid is of sufficient volume to completely fill the void volume of the exposed membrane such that the total surface area of the membrane and all antibody or receptor zones are contacted by the fluid. Such a device would also incorporate, if necessary, a means for removal of unbound conjugates from the membrane and a means for contacting the conjugates bound to immobilized antibodies or receptors on the membrane with materials needed to develop the signals associated with the signal development elements.

Clearly, the use of the method of the present invention with such devices would provide one with the ability to assay for multiple target ligands in a single sample using a single test device. In the multiple, simultaneous ligand-receptor assay formats a solid support comprising for each target ligand to be determined, at least one discrete reaction zone on which is localized either receptor specific for target ligand or antibody specific for the complex of ligand receptor and ligand or both.

The antibody conjugate can be used in a variety of assay processes for the determination of the target ligand concentration in fluid samples. The sample can be contacted with the antibody conjugate first and then contacted with the ligand receptor to form the assay mixture. Alternatively, the sample can be contacted with the ligand receptor before contact with the antibody conjugate. The antibody conjugate can also be mixed with the ligand receptor prior to contact of the mixture with the sample. After these three elements of the assay mixture have been contacted with one another for sufficient time so that the amount of the antibody conjugate-ligand receptor-ligand complex that is formed is related to the concentration of the target ligand in the sample, the unbound antibody conjugate is separated from the bound fraction. Precipitation or immobilization of the ligand receptor on a solid phase facilitates this separation. Normally, a wash step is required to remove the unbound antibody conjugate from the bound fraction. The selection and use of antibodies also having an affinity for the complex of ligand receptor and target ligand that is 1000× greater than the affinity of the antibody for the target ligand is the best mode for practicing this invention. In a particularly preferred embodiment, enzyme channeling methods such as those described in U.S. Pat. No. 4,233,402 are utilized in conjunction with a solid phase as described in U.S. Pat. No. 4,391,904 so that no washing step is necessary. In assay processes requiring the removal of the unbound antibody conjugate, the presence of the antibody conjugate-ligand receptor-ligand complex is detected by adding any additional reagents, if necessary, to generate a signal from the signal development element. For example, if the signal development element is an enzyme, a suitable substrate is added and the formation of the product can be monitored with a spectrophotometer. The use of signal development elements that are visible, such as colloidal gold, eliminates the need for additional reagents to develop the response.

Alternatively, the ligand receptor can be labeled for detection by formation of a ligand receptor conjugate where the ligand receptor is coupled directly or indirectly to a signal development element. When the antibody is bound to ligand receptor conjugate-ligand complexes, the amount of antibody-ligand receptor conjugate-ligand complex is related to the concentration of target ligand in the sample. The selection and use of antibodies having an affinity for the complex of ligand receptor conjugate and target ligand that is 1000× greater than the affinity of the antibody for the target ligand is the best mode for practicing this invention. A preferred embodiment is one where the antibody is bound to a solid phase to facilitate removal of the unbound ligand receptor conjugate from the assay mixture by washing. Alternatively, the antibody and moieties bound to it, such as the complex of ligand receptor conjugate and ligand, can be separated from the assay mixture by utilizing an immobilized receptor for the antibody. The antibody can also be coupled to a hapten or another element for which there is a specific receptor, such as an anti-hapten antibody. The specific receptor can then be used to remove the antibody and moieties bound to it from the assay mixture. These methods, depending upon assay design, can each be utilized successfully to develop assays where the amount of antibody conjugate-ligand receptor conjugate-ligand complex is detected and related to the concentration of target ligand in the sample. When antibodies are used that are selected according to the teachings of the present invention in the assay formats described, the "hook" effect is substantially eliminated.

The antibody and the ligand receptor conjugate can be used in a variety of assay processes for the determination of the target ligand concentration in fluid samples. The sample can be contacted with the ligand receptor conjugate first and then contacted with the antibody to form the assay mixture. Alternatively, the sample can be contacted with the antibody before contact with the ligand receptor conjugate. The antibody can also be mixed with the ligand receptor conjugate prior to contact of the mixture with the sample. After these three elements of the assay mixture have been contacted with one another for sufficient time so that the amount of the antibody-ligand receptor conjugate-ligand complex that is formed is related to the concentration of the target ligand in the sample, the unbound ligand receptor conjugate is separated from the bound fraction. Precipitation or immobilization of the antibody on a solid phase facilitates this separation. Normally, a wash step is required to remove the unbound ligand receptor conjugate from the bound fraction. In a particularly preferred embodiment, enzyme channeling methods such as those described in U.S. Pat. No. 4,233,402 are utilized in conjunction with a solid phase as described in U.S. Pat. No. 4,391,904 so that no washing step is necessary. In assay processes requiring the removal of the unbound ligand receptor conjugate, the presence of the antibody-ligand receptor conjugate-ligand complex is detected by adding any additional reagents, if necessary, to generate a signal from the signal development element. For example, if the signal development element is an enzyme, a suitable substrate is added and the formation of the product can be monitored with a spectrophotometer. The use of signal development elements that are visible, such as colloidal gold, eliminates the need for additional reagents to develop the response.

The present invention is particularly useful in non-competitive ligand-receptor assays where the ligand concentration can exceed the concentration of the ligand receptors and cause a "hook" effect. Target ligands that commonly pose "hook" problems for the designers of immunometric sandwich assays include HCG (human chorionic gonadotropin), Hepatitis B Surface Antigen, and albumin in urine. However, in sandwich assays for all target ligands where the sample and the labeled and unlabeled ligand receptors are incubated simultaneously, the assay can be improved by the use of the present invention. Even before the concentration of the target ligand exceeds the concentration of the ligand receptors used in the assay, separate target ligands can bind to both the ligand receptor and the labeled ligand receptor to inhibit the formation of the ligand receptor-target ligand-labeled ligand receptor complex that is necessary to detect the amount of target ligand in the sample. The response of a sandwich assay is typically not a linear function of the target ligand concentration except over the lower range of target ligand concentration due to this inhibiting effect. Because the antibody has a very low affinity for the target ligand, the inhibiting effect of the target ligand is eliminated. Thus, use of the present invention will result in a linear assay response over a substantially larger range of target ligand concentration than previous assays. only two standards are needed to calibrate the linear assay response so that calibration is simplified.

Assays for specific DNA or RNA sequences rely upon hybridization of a oligonucleotide probe with the target ligand. Antibodies that bind the complex of oligonucleotide probe and target ligand but do not bind the oligonucleotide probe in amounts that are detectable above the assay response noise as a result of the assay process can be used to detect the presence or amount of such target ligands. The use of Polymerase Chain Reaction methods has extended the sensitivity of oligonucleotide probe assays by amplifying the number of copies of the target sequence. Such amplification in an unknown sample can lead to a large concentration of target sequences in excess over the concentration of oligonucleotide probe. The use of antibodies to bind the complex of the probe and the target sequence according to the present invention simplifies the design of such assays by increasing the range of probe concentration that can be used and by providing a rapid and efficient capture mechanism for the detection of probe-target sequence hybrids.

We claim:

1. A device for performing an assay to detect the presence of a target ligand in a sample, said device comprising:

a first receptor immobilized to a surface of the device, wherein the affinity of the first receptor for a complex of a target ligand and a second receptor is at least ten times as great as the affinity of the first receptor for the target ligand alone, and wherein said device is adapted and arranged such that the assay, when performed, is essentially unaffected by a hook effect.

2. The device of claim 1, further comprising a second receptor, said second receptor able to bind the target ligand to form a complex during performance of the assay.

3. The device of claim 2 further comprising a means for contacting the first receptor with the complex.

4. The device of claim 1 further comprising a means for placing the sample in contact with the first receptor.

5. The device of claim 2 wherein the second receptor is conjugated to a signal development element to form a receptor conjugate.

6. The device of claim 5 further comprising a means for removing nonbound second receptor from the presence of the complex.

7. The device of claim 1 wherein the first receptor has an affinity for the complex that is at least 100 times as great as the affinity of the first receptor for the target ligand.

8. The device of claim 7 wherein the first receptor has an affinity for the complex that is at least 1000 times as great as the affinity of the first receptor for the target ligand.

9. A device for performing an assay to detect the presence of a target ligand in a sample, said device comprising:

a first receptor immobilized to a surface of the device, said first receptor able to bind the target ligand to form a complex;

a second receptor, said second receptor capable of binding the complex, wherein the affinity of the second receptor for the complex is at least ten times as great as the affinity of the second receptor for the target ligand;

a means for contacting the second receptor with the complex when complex has been formed, wherein said device is adapted and arranged such that the assay, when performed, is essentially unaffected by a hook effect.

10. The device of claim 9 further comprising a means for placing sample in contact with the first receptor.

11. The device of claim 9 wherein the second receptor is conjugated to a signal development element to form a receptor conjugate.

12. The device of claim 11 further comprising a means for removing nonbound second receptor from the presence of the complex.

13. The device of claim 9 wherein the second receptor capable of binding the complex has an affinity for the complex that is at least 100 times as great as the affinity of the second receptor for the target ligand.

14. The device of claim 13 wherein the second receptor capable of binding the complex has an affinity for the complex that is at least 1000 times as great as the affinity of the second receptor for the target ligand.

15. A device for performing an assay to detect the presence of a target ligand in a sample, said device comprising:
   a first receptor coupled to a signal development element, said first receptor capable of binding the target ligand to form a complex;
   a second receptor, said second receptor capable of binding the complex, wherein the affinity of the second receptor for the complex is at least ten times as great as the affinity of the second receptor for the target ligand; and,
   a third receptor immobilized to a surface of the device, said third receptor capable of binding the second receptor when it is bound to the complex, wherein said device is adapted and arranged such that the assay, when performed, is essentially unaffected by a hook effect.

16. The assay device of claim 15 further comprising a means for contacting the third receptor with the complex when complex has been formed.

17. A kit for use in conducting an assay that is essentially unaffected by a hook effect, where the assay determines the presence or amount of a target ligand, said kit comprising:
   a first receptor, said first receptor capable of binding the target ligand to form a complex; and,
   a second receptor, said second receptor capable of binding the complex, wherein the affinity of the second receptor for the complex is at least ten times as great as the affinity of the second receptor for the target ligand;
   wherein said kit is adapted and arranged such that the assay, when performed, is essentially unaffected by a hook effect.

18. The kit of claim 17, further comprising an assay device capable of containing the first receptor, the second receptor and the sample during performance of the assay.

19. The kit of claim 18, where the first receptor is immobilized to a surface of the assay device.

20. The kit of claim 18, where the second receptor is immobilized to a surface of the assay device.

21. The kit of claim 14, wherein the device comprises a means for placing sample in contact with the first receptor, whereby complex can be formed when target ligand is in the sample.

22. The kit of claim 18, wherein the device comprises a means for contacting the second receptor with the complex when complex has been formed.

23. The kit of claim 19, wherein the second receptor is conjugated to a signal development element to form a receptor conjugate, and wherein the device comprises a means for removing the receptor conjugate which is non-bound to the complex from the presence of receptor conjugate bound to the complex.

24. The kit of claim 20, wherein the first receptor is conjugated to a signal development element to form a receptor conjugate, and wherein the device comprises a means for removing the receptor conjugate which is non-bound to the complex from the presence of receptor conjugate bound to the complex.

25. The kit of claim 18, wherein the first receptor is conjugated to a signal development element to create a receptor conjugate, and wherein a third receptor is immobilized to a surface of the assay device, said third receptor capable of binding the second receptor, whereby a complex of the first receptor and the target ligand can become attached to the device by binding of the complex to the second receptor which is then bound to the device by the third receptor.

26. The kit of claim 18, wherein the second receptor is conjugated to a signal development element to create a receptor conjugate, and wherein a third receptor is immobilized to a surface of the assay device, said third receptor capable of binding the first receptor, whereby a complex of the first receptor and the target ligand can become attached to the device by binding of the first receptor in the complex to the third receptor.

27. The kit of claim 17, wherein the first receptor, the second receptor, or the first and second receptors is/are antibodies.

28. A test device for performing an assay to determine the presence or amount of at least one target ligand in a fluid sample suspected of containing said target ligand, said target ligand capable of binding to a ligand receptor conjugate and to an antibody immobilized to a surface of the device, said device further comprising:
   a. a means for contacting said fluid sample with said ligand receptor conjugate and the immobilized antibody, said antibody capable of binding the complex of said target ligand and said ligand receptor conjugate, the binding affinity of said antibody for said complex being at least a factor of 10 greater than the affinity of said antibody for said target ligand, wherein no detectable assay response results from the binding of antibody and ligand receptor conjugate in the absence of target ligand, wherein the amount of ligand receptor conjugate bound to antibody is related to the amount of target ligand in the fluid sample;
   b. a means for detecting said complex bound to said antibody; and,
   c. a means for relating the presence or amount of complex detected to the presence or amount of said target ligand in said fluid sample, wherein said device is adapted and arranged such that the assay, when performed, is essentially unaffected by a hook effect.

29. The device of claim 28 further comprising a means for contacting the fluid from step (a) with a means for removing said ligand receptor conjugate which is nonbound to complex from said fluid.

30. A test device for performing an assay to determine the presence or amount of at least one target ligand in a fluid sample suspected of containing said target ligand, said target ligand capable of binding to a ligand receptor immobilized on a surface of the device and an antibody conjugate, said device further comprising:
   a. a means for contacting said fluid sample with said immobilized ligand receptor and said antibody conjugate, said antibody conjugate capable of binding the complex of said target ligand and said ligand receptor, the binding affinity of said antibody conjugate for said complex being at least a factor of 10 greater than the affinity of said antibody conjugate for said target ligand, wherein no detectable assay response results from the binding of antibody conjugate and ligand receptor in the absence of target ligand, and wherein the amount of ligand receptor bound to antibody conjugate is related to the amount of target ligand in the fluid sample;
   b. a means for detecting said complex bound to said antibody conjugate; and,
   c. a means for relating the presence or amount of complex detected to the presence or amount of said target ligand in said fluid sample, wherein said device is adapted and arranged such that the assay, when performed, is essentially unaffected by a hook effect.

31. The device of claim 30, further comprising a means for contacting the fluid from step (a) with a means for removing said antibody conjugate which is nonbound to complex from said fluid.

32. A test device for performing an assay to determine the presence or amount of at least one target ligand in a fluid sample suspected of containing said target, said target ligand capable of binding to a ligand receptor and to an antibody conjugate, said device comprising:

a. a means for contacting said fluid sample with said ligand receptor and said antibody conjugate, said antibody conjugate capable of binding a complex of said target ligand and said ligand receptor, the binding affinity of said antibody conjugate for said complex being at least a factor of 10 greater than the affinity of said antibody conjugate for said target ligand, wherein no detectable assay response results from the binding of antibody conjugate and ligand receptor in the absence of target ligand, wherein the amount of antibody conjugate bound to ligand receptor is related to the amount of target ligand in the fluid sample;
   b. a receptor immobilized to a surface of the device, the immobilized receptor capable of binding ligand receptor when ligand receptor is bound to the target ligand having formed a complex;
   c. a means for detecting said antibody conjugate bound to said complex; and,
   d. a means for relating the presence or amount of complex detected to the presence or amount of target ligand in said fluid sample, wherein said device is adapted and arranged such that the assay, when performed, is essentially unaffected by a hook effect.

33. The device of claim 32, further comprising a means for contacting the fluid from step (a) with a means for removing antibody conjugate which is nonbound to the complex from said fluid.

34. The device of claim 1, wherein said first receptor is an antibody or an antibody fragment selected to substantially eliminate the hook effect.

35. The device of claim 9, wherein said second receptor is an antibody or an antibody fragment selected to substantially eliminate the hook effect.

36. The device of claim 15, wherein said second receptor is an antibody or an antibody fragment selected to substantially eliminate the hook effect.

37. The kit of claim 17, wherein said second receptor is an antibody or an antibody fragment selected to substantially eliminate the hook effect.

38. The device of claim 28, wherein said antibody is selected to substantially eliminate the hook effect.

39. The device of claim 30, wherein said antibody conjugate is selected to substantially eliminate the hook effect.

40. The device of claim 32, wherein said antibody conjugate is selected to substantially eliminate the hook effect.

* * * * *